United States Patent [19]

Papenfuhs et al.

[11] Patent Number: 4,754,071
[45] Date of Patent: Jun. 28, 1988

[54] PROCESS FOR PREPARING ARYL HYDROXYETHYL SULFONES

[75] Inventors: Theodor Papenfuhs, Frankfurt am Main; Wolfgang Koller, Sulzbach; Walter Kühn, Hofheim am Taunus, all of Fed. Rep. of Germany

[73] Assignee: Hoechst Aktiengesellschaft, Frankfurt am Main, Fed. Rep. of Germany

[21] Appl. No.: 927,730

[22] Filed: Nov. 5, 1986

[30] Foreign Application Priority Data

Nov. 7, 1985 [DE] Fed. Rep. of Germany ....... 3539477

[51] Int. Cl.$^4$ ............................................. C07C 147/10
[52] U.S. Cl. ..................................................... 568/32
[58] Field of Search .......................................... 568/32

[56] References Cited

U.S. PATENT DOCUMENTS 3,016,403  1/1962  Dodson ................................ 568/32
3,092,672  6/1963  Klass .................................. 585/425
4,613,704  9/1986  Papenfuhs ........................... 564/418

FOREIGN PATENT DOCUMENTS 3343421  6/1985  Fed. Rep. of Germany .

Primary Examiner—Mary E. Ceperley
Attorney, Agent, or Firm—Connolly & Hutz

[57] ABSTRACT

Process for preparing aryl hydroxyethyl sulfones of the general formula (1)

$$Ar-SO_2-CH_2-CH_2-OH \qquad (1)$$

in which Ar denotes a phenyl or naphthyl radical, by reacting an aromatic of the formula (2)

$$Ar-H \qquad (2)$$

in which Ar has the abovementioned meanings, with carbyl sulfate at temperatures of 30° to 100° C., in the presence or absence of an organic solvent which is inert toward the reactants, then adding water or methanol to decompose the boron trichloride, and isolating the resulting aryl hydroxyethyl sulfone.

4 Claims, No Drawings

PROCESS FOR PREPARING ARYL HYDROXYETHYL SULFONES

The present invention relates to a one-stage process for preparing aryl hydroxyethyl sulfones which are important intermediates for preparing reactive dyes of the vinyl sulfone series.

Phenyl hydroxyethyl sulfones of the general formula (I)

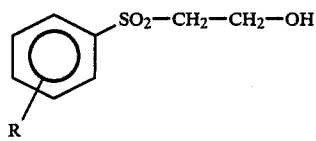

in which R denotes a hydrogen atom or an alkyl group, have hitherto been prepared by two known processes which are each characterized by at least two synthesis steps.

One process comprises sulfochlorinating aromatics of the formula (II) to give the compounds of the formula (III), reducing these to the sulfinic acids of the formula (IV) and ethoxylating the latter to give the sulfones of the formula (I) in accordance with the reaction diagram

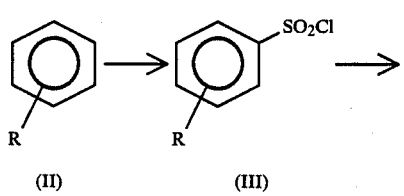

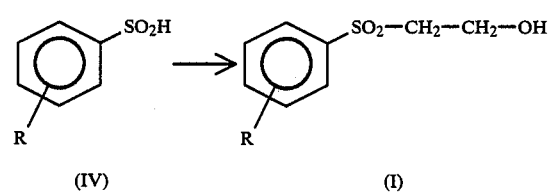

(cf. for example European Preliminary Published Application No. 0,115,328).

The other known process comprises replacing halogen in activated aromatics of the formula (V) for a mercaptoethanol radical to give the sulfides of the formula (VI) and oxidizing the latter to give the sulfones of the formula (I) in accordance with the reaction diagram

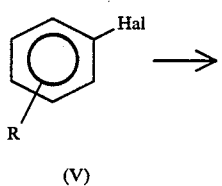

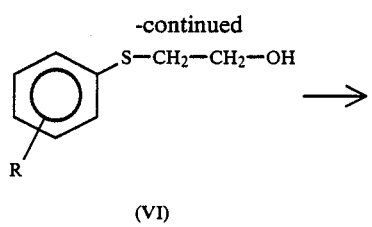

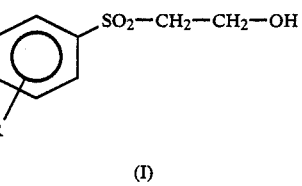

(cf. for example German Offenlegungsschrift 3,343,421).

The two aforementioned, known multi-stage processes for preparing aryl hydroxyethyl sulfones of the formula (I) are practiced in industry. Single-stage processes for introducing the hydroxyethylsulfonyl group, however, have hitherto not been disclosed.

U.S. Pat. No. 3,092,672 reveals that reacting benzene or alkyl-substituted benzenes or condensed aromatic ring systems with carbyl sulfate in the presence of Friedel-Crafts catalysts leads not, as might be imagined, to compounds of the formula (I) in accordance with the reaction diagram

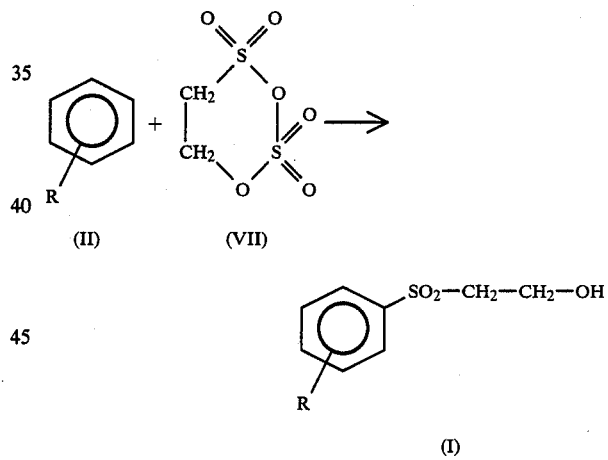

but to diarylethane derivatives.

It has now been found, surprisingly, that aryl hydroxyethyl sulfones of the general formula (1)

$$Ar-SO_2-CH_2-CH_2-OH \quad (1)$$

in which Ar denotes a phenyl or naphthyl radical, can be prepared in an advantageous manner in a single-stage process by reacting an aromatic of the general formula (2)

$$Ar-H \quad (2)$$

in which Ar has the abovementioned meanings, with carbyl sulfate in the presence of boron trichloride at temperatures of 30° to 100° C., preferably 40° to 60° C., in the presence or absence of an organic solvent which is inert toward the reactants, then adding water or methanol to decompose the boron trichloride, and isolating the resulting aryl hydroxyethyl sulfone of the formula (1).

It is expedient to use aromatic (benzene or naphthalene) and carbyl sulfate in a molar ratio of 1:1, yet the molar ratio can be varied from 1:2 to 5:1.

The boron trichloride is to be used in a molar ratio of at least 1:1, based on the carbyl sulfate; however, it can also be used in a molar excess of up to 2:1, although this will bring only a moderate increase in yield.

Organic solvents which are inert toward the reactants carbyl sulfate and boron trichloride are aromatic hydrocarbons, such as benzene (which is not eligible in the case of the reaction with naphthalene, in order to avoid obtaining mixed products), aliphatic or cycloaliphatic hydrocarbons, such as octane, its isomers or cyclohexane, and also halogenated, preferably chlorinated, aromatic hydrocarbons, such as chlorobenzene or dichlorobenzene, halogenated, preferably chlorinated, aliphatic hydrocarbons, such as dichloromethane, dichloroethane or propyl chloride.

While if benzene is used as a starting compound the addition of an inert organic solvent is not absolutely necessary, such an addition is required when naphthalene is the starting compound used.

Suitable for isolating the desired end products by extraction are for example alkyl$C_1$–$C_4$ alkyl$C_1$–$C_3$-carboxylates, such as ethyl, propyl or butyl acetate, or aromatic hydrocarbons, such as benzene, toluene or xylenes, or halogenated aromatic hydrocarbons, such as chlorobenzene or dichlorobenzene, or ketones such as methyl isobutyl ketone.

It is expedient to carry out the reaction by introducing into a suspension of carbyl sulfate in the aromatic a solution of boron trichloride in an inert organic solvent dropwise or the boron trichloride directly in gas form, and after the reaction has ended decomposing the catalyst with water or methanol. In the decomposition of boron trichloride with water, it can be expedient to add a neutralizing agent, such as, for example, sodium hydrogencarbonate, as well. The reaction time varies between 30 minutes and two hours.

The isolation of the end products, which is possible by chromatography, is preferably effected by extraction.

EXAMPLE 1

A solution of 47 parts of boron trichloride in 312 parts of dichloroethane is added dropwise at 40°–60° C. to a suspension of 75.2 parts of carbyl sulfate in 78 parts of benzene in the course of 20 minutes. This is followed by 30 minutes of stirring, after which 150 parts of water, 47 parts of sodium hydrogencarbonate and 100 parts of ethyl acetate are added. The resulting precipitate is then filtered off, and after the phases have been separated, the aqueous phase is washed twice with 100 parts of ethyl acetate. Removal of the solvent by distillation leaves 43.4 parts of phenyl hydroxyethyl sulfone, which corresponds to a yield of 58% of theory.

EXAMPLE 2

Example 1 is repeated, except that, instead of ethyl acetate, methyl isobutyl ketone is used for the extraction, affording 42 parts of phenyl hydroxyethyl sulfone, which corresponds to a yield of 56% of theory.

EXAMPLE 3

A solution of 47 parts of boron trichloride in 312 parts of dichloroethane is added dropwise to a mixture of 12.8 parts of naphthalene and 37.6 parts of carbyl sulfate in the course of 15 minutes. This is followed by heating to 30°–45° C. for 1 hour and then refluxing for half an hour. 100 parts of methanol are then added, refluxing is continued for a further 30 minutes, and the solvent is distilled off. The bottom product yields after chromatography over silica gel in chlorobenzene/dimethylformamide (2:1) 13 parts of 1-naphthyl hydroxyethyl sulfone, which corresponds to a yield of 55% of theory.

EXAMPLE 4

Example 3 is repeated, except that 100 parts of cyclohexane are added as solvent for naphthalene, affording 12.5 parts of 1-naphthyl hydroxyethyl sulfone, which corresponds to a yield of 53% of theory.

We claim:
1. A process for preparing aryl hydroxyethyl sulfones of the formula (1)

$$Ar-SO_2-CH_2-CH_2-OH \quad (1)$$

in which Ar denotes a phenyl or naphthyl radical, which comprises reacting an aromatic of the formula (2)

$$Ar-H \quad (2)$$

in which Ar has the abovementioned meanings, with carbyl sulfate in the presence of boron trichloride at temperatures of 30° to 100° C., in the presence or absence of an organic solvent which is inert toward the reactants, then adding water or methanol to decompose the boron trichloride, and isolating the resulting aryl hydroxyethyl sulfone.

2. The process as claimed in claim 1, wherein the reaction is carried out at temperatures of 40° to 60° C.

3. The process as claimed in claim 1, wherein the reaction is carried out in benzene, octane, cyclohexane, chlorobenzene, dichlorobenzene, dichloromethane, dichloroethane or propyl chloride as inert organic solvent.

4. The process as claimed in claim 1, wherein the reaction product is isolated by extracting with ethyl, propyl, or butyl acetate, benzene, toluene, xylenes, chlorobenzene, dichlorobenzene or methyl isobutyl ketone.

* * * * *